US009168398B2

(12) United States Patent
Hattendorf et al.

(10) Patent No.: US 9,168,398 B2
(45) Date of Patent: Oct. 27, 2015

(54) SKIN TREATMENT COMPOSITIONS

(75) Inventors: Judy Hattendorf, Marina Del Ray, CA (US); Steve Carlson, San Mateo, CA (US)

(73) Assignee: OMP, INC., Irvine, CA (US)

( * ) Notice: Subject to any disclaimer, the term of this patent is extended or adjusted under 35 U.S.C. 154(b) by 114 days.

(21) Appl. No.: 12/743,127

(22) PCT Filed: Nov. 14, 2008

(86) PCT No.: PCT/US2008/083590
§ 371 (c)(1),
(2), (4) Date: Aug. 3, 2010

(87) PCT Pub. No.: WO2009/065008
PCT Pub. Date: May 22, 2009

(65) Prior Publication Data
US 2010/0303747 A1    Dec. 2, 2010

Related U.S. Application Data

(60) Provisional application No. 61/003,015, filed on Nov. 14, 2007.

(51) Int. Cl.
*A61Q 19/02*    (2006.01)
*A61K 8/60*    (2006.01)

(52) U.S. Cl.
CPC ............... *A61Q 19/02* (2013.01); *A61K 8/602* (2013.01)

(58) Field of Classification Search
USPC .............................................. 424/401; 42/62
See application file for complete search history.

(56) References Cited

U.S. PATENT DOCUMENTS

| | | | |
|---|---|---|---|
| 4,229,427 A | 10/1980 | Whitehouse | |
| 5,747,006 A * | 5/1998 | Dornoff et al. | 424/62 |
| 5,976,555 A | 11/1999 | Liu et al. | |
| 6,280,754 B1 * | 8/2001 | Hanada et al. | 424/401 |
| 6,497,860 B1 * | 12/2002 | Kawato et al. | 424/62 |
| 7,431,949 B2 * | 10/2008 | Neis et al. | 424/725 |
| 2001/0053350 A1 | 12/2001 | Chevalier et al. | |
| 2003/0215471 A1 * | 11/2003 | Wilmott et al. | 424/401 |
| 2004/0042984 A1 | 3/2004 | Park et al. | |
| 2005/0118119 A1 | 6/2005 | Stoltz et al. | |
| 2006/0251598 A1 * | 11/2006 | Ramirez et al. | 424/70.1 |
| 2007/0048234 A1 | 3/2007 | Waugh et al. | |
| 2007/0134178 A1 * | 6/2007 | Obioha et al. | 424/62 |
| 2007/0154503 A1 * | 7/2007 | Hattendorf et al. | 424/401 |
| 2007/0207110 A1 | 9/2007 | Neis et al. | |
| 2007/0269534 A1 | 11/2007 | Ramirez et al. | |

FOREIGN PATENT DOCUMENTS

| | | | |
|---|---|---|---|
| EP | 0692243 A1 | 1/1996 | |
| FR | 2577805 A1 | 8/1986 | |
| JP | 60-056912 A2 | 4/1985 | |
| JP | 61-207316 A2 | 9/1985 | |
| JP | 61-200906 A2 | 9/1986 | |
| JP | 61-210009 A2 | 9/1986 | |
| JP | 60-016906 A2 | 1/1995 | |
| JP | 63-008314 A2 | 1/1998 | |
| JP | 02-142714 A | 5/2002 | |
| JP | 03-058326 A | 2/2003 | |
| JP | 2005120032 A * | 5/2005 | |
| JP | 2007-204475 A | 8/2007 | |
| WO | 03/082238 A1 | 10/2003 | |
| WO | WO 2007/054977 A2 | 5/2007 | |
| WO | WO 2007/106501 A2 | 9/2007 | |

OTHER PUBLICATIONS

Yamamoto, Y. et al. "External Preparation for Skin", English translation of JP 2005120032, May 12, 2005, PTO-1405236.*
Chardon et al., "Skin colour typology and suntanning pathways", Int. J Cosmet Sci 1991; 13(4):191-208 (Abstract only).
Maeda et al., Arbutin: Mechanism of its Depigmenting Action in Human Melanocyte Culture, Journal of Pharmacology and Experimental Therapeutics, Feb. 1996; 276: 765-769.
El-Domyati et al., Intrinsic aging vs. photoaging: a comparative histopathological, immuno-histochemical, and ultrastructural study of skin, Experimental Dermagology 2002: 11: 398-405.
Clarys et al., Skin color measurements: comparison between three instruments: the Chromameter®, the DermaSpectrometer® and the Mexameter®, Skin Research and Technology 2000; 6: 230-238.
Palumbo et al., "Skin Depigmentation by Hydroquinone: A Chemical and Biochemical Insight", Pigment Cell Search Suppl. 2: 299-303 (1992).
Herndon et al., "Efficacy of a Tretinoin/Hydroquinone-Based Skin Health System in the Treatment of Facial Photodamage", Costmetic Dermagology, Apr. 2006, vol. 19, No. 4, p. 255-263.
Database GNPD, MINTEL; Sep. 2007, "Skincare Products" XP002726243, Database accession No. 751758 * "Ingredients" *.
Database GNPD, MINTEL; Sep. 2004, "White Lucent Concentrated Brightening Serum" XP002726244, Database accession No. 301582 * "Ingredients" *.
Database GNPD, MINTEL; Jul. 2004, "Brightening Cleanser" XP002726245, Database accession No. 10178476 * "Ingredients" *.
Ketsuhingaku, Shinka, "Lotion," Jan. 18, 2001, p. 354-356, 383-387, 384.

* cited by examiner

*Primary Examiner* — Gina Justice

(74) *Attorney, Agent, or Firm* — Kilpatrick Townsend & Stockton LLP

(57) ABSTRACT

Arbutin-containing compositions are useful for topical application to provide enhanced luminosity, brightening or lightening to the skin of a user and are at least 85% as efficacious (with regard to skin lightening, when used alone or in a system as measured by Chromameter® b* parameter values) as substantially corresponding compositions containing hydroquinone in an amount from about the same molar amount to about 1.5 times the molar amount of arbutin.

4 Claims, 3 Drawing Sheets

SKIN TREATMENT COMPOSITIONS

CROSS-REFERENCE TO RELATED APPLICATIONS

This application is a U.S. National Stage Application filed under 35 U.S.C. §371(a) of International Application No. PCT/US2008/083590, which claims the benefit of and priority to U.S. Provisional Application No. 61/003,015, filed on Nov. 14, 2007.

Arbutin-containing compositions in accordance with the present disclosure are useful for topical application to provide enhanced luminosity, brightening or lightening to the skin of a user. The present arbutin-containing compositions are at least 85% as efficacious (with regard to skin lightening, when used alone or in a system as measured by Chromameter® b* parameter values) as substantially corresponding compositions containing hydroquinone in an amount from about the same molar amount to about 1.5 times the molar amount of arbutin. By "substantially corresponding" it is meant that the compositions contain the same ingredients in amounts that may be adjusted to equate viscosity, where necessary.

In embodiments, compositions of the present disclosure contain arbutin and a unique mixture of ingredients that may include an aqueous phase and an oil phase. As used herein the term arbutin means hydroxy phenyl-b-D-glucopyranoside, a well-known compound having the general formula:

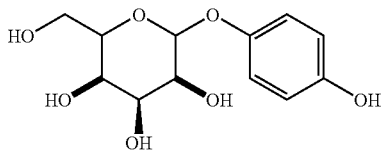

Arbutin is essentially hydroquinone with a D-glucose molecule attached. Arbutin competitively inhibits tyrosinase but does not inhibit cellular function.

The arbutin is present in amounts that provide a benefit to the skin of a user. In embodiments, arbutin is present in an amount sufficient to effect depigmentation. Generally, arbutin in amounts from about 1 to about 20% by weight of the total composition is suitable. In embodiments, arbutin is present in an amount of at least about 5% by weight of the composition, in embodiments from about 5 to about 10% by weight of the total composition.

The aqueous phase may include water, one or more humectants, one or more emulsifiers, one or more preservatives, one or more chelating agents, one or more reducing agents and one or more pH adjusters. Purified water can advantageously be used, such as, for example, de-ionized water or USP water.

Suitable preservatives for the aqueous phase include, but are not limited to methylparaben, sodium butylparaben, benzoic acid and its salts and esters, benzyl alcohol, urea derivatives such as diazolidinyl urea, imidazolidinyl urea, and 2,3-Imidazolidinedione (DMDM hydantoin), sorbic acid and its salts, and the like. Typically, the one or more preservatives are present in an amount from about 0.01 to about 5% by weight of the total composition, with individual preservatives being present in an amount from about 0.005% to about 5% by weight of the composition. In embodiments, the preservatives are present in an amount from about 0.05 to about 1% by weight of the total composition.

Suitable chelating agents for the use in the aqueous phase include, but are not limited to edetate disodium, EDTA (ethylenediaminetetraacetic acid) and its salts, for example, trisodium NTA (nitrilotriacetic acid), etidronic acid and its salts, sodium dihydroxyethylglycinate, citric acid and its salts, and combinations thereof. Typically, the amount of chelating agent(s) is from about 0.01 to about 5% by weight of the total composition. In embodiments, the one or more chelating agents are present in an amount of about 0.05 to about 1% by weight of the total composition. In embodiments, a combination of chelating agents is present, with each individual chelating agent being present in an amount from about 0.005% to about 0.5% by weight of the composition.

Suitable humectants for use in the aqueous phase include, but are not limited to polyhydric alcohols including glycerin, diglycerin, triglycerin, polyglycerin, polypropylene glycol, polyethylene glycol, ethylene glycol, diethylene glycol, triethylene glycol, propylene glycol, dipropylene glycol, hexylene glycol, 1,3-butylene glycol, 1,4-butylene glycol, ethylene glycol monoalkyl ether, diethylene glycol monoalkyl ether, glucose, maltose, sucrose, lactose, xylitose, xylitol, sorbitol, mannitol, maltitol, panthenol, pentaerythritol, and hyaluronic acid and its salts. It should, of course be understood that combinations of two or more humectants can be included in the present compositions. Typically, the one or more humectants are present in an amount from about 1 to about 20% by weight of the total composition. In embodiments, humectants are present in an amount from about 2 to about 5% by weight of the total composition. In embodiments, a combination of humectants is present, with each individual humectant being present in an amount from about 0.5% to about 5% by weight of the composition.

Suitable emulsifiers for use in the aqueous phase are surfactants. Useful surfactants can be ionic or nonionic, and they can be used alone or in admixture. Illustrative examples of suitable surfactants include cetearyl alcohol and sodium cetearyl sulfate, PEG-1000 monocetyl ether, or quaternary ammonium salts such as alkyl trimethyl ammonium bromide; polyol ester glycerol monostearate and potassium stearate, sodium lauryl sulfate (SLS), and ethoxylated fatty alcohols constitute good coemulsifiers. Fatty acids like stearic acids may be included to regulate the consistency of the emulsion. Optionally, polymers such as carbomers also can be included. Particularly useful emulsifiers for use in the aqueous phase are sodium lauryl sulfate, saponins or combinations thereof. Typically, the one or more emulsifiers are present in an amount from about 1 to about 20% by weight of the total composition. In embodiments, the emulsifiers are present in an amount from about 2 to about 5% by weight of the total composition. In embodiments, a combination of emulsifiers is present, with each individual emulsifier being present in an amount from about 0.005% to about 4% by weight of the composition.

The pH of the aqueous phase can be adjusted to be about 2 to 4, such that the final product has a pH such as between about 2 to 4. Agents suitable for adjusting the pH of the aqueous phase include, but are not limited to citric acid, phosphoric acid, lactic acid or glycolic acid. Typically, the one or more pH adjustment agents are present in an amount from about 0.01 to about 5% by weight of the total composition. In embodiments, the pH adjustment agents are present in an amount from about 0.1 to about 1.0% by weight of the total composition. In embodiments, a combination of pH adjustment agents is present, with each individual pH adjustment agent being present in an amount from about 0.005% to about 1% by weight of the composition.

Suitable reducing agents for use in the present compositions include, but are not limited to ascorbic acid, propyl gallate and sulfites, including but not limited to sulfites, bisulfites, metabisulfites, their salts, and their derivatives. Sodium metabisulfite is one useful sulfite. Since arbutin has a tendency to discolor through oxidation, these reducing agents can be advantageously used because they have greater tendencies to oxidize than arbutin. Sodium metabisulfite has the added advantage that it does not discolor by oxidation. In arbutin and sodium metabisulfite compositions, it is believed that the sodium metabisulfite oxidizes first and delays the start of any oxidation of the arbutin, so that excessive discoloration is delayed or totally avoided. Typically, the one or more reducing agents are present in amounts from about 0.1 to about 10% by weight of the total composition. In embodiments, the reducing agents are present in an amount from about 0.25 to about 5% by weight of the total composition. In embodiments, a combination of reducing agents is present, with each individual reducing agent being present in an amount from about 0.005% to about 1% by weight of the composition.

The aqueous phase can be prepared by combining the various ingredients while mixing with heating (e.g., from about 70° C. to about 75° C.).

The aqueous phase can be mixed with an oil phase. The oil phase may include one or more emollients, one or more preservatives and one or more antioxidants.

Suitable emollients for use in the oil phase include cosmetically acceptable liquid oils. The cosmetically acceptable liquid oil is liquid at room temperature. The cosmetically acceptable liquid oil can be liquid hydrocarbon oil, liquid natural oil, liquid fatty alcohol, liquid fatty acid, liquid fatty acid ester, liquid silicone oil, and paste wax and mixtures thereof.

Non-limiting examples of the liquid hydrocarbons suitable for use in the oil phase include squalane, liquid mineral oil, and liquid polybutene. Non-limiting examples of the liquid natural oil derived from plants useful in the present compositions include almond oil, olive oil, sesame oil, safflower oil, avocado oil, cottonseed oil, jojoba oil, castor oil, soybean oil, palm kernel oil, coconut oil, and hydrogenated vegetable oil. Non-limiting examples of the liquid natural oil derived from animal sources useful in the present compositions include mink oil and egg yolk oil. Non-limiting examples of the liquid fatty alcohol useful in the present compositions are isostearyl alcohol, lanolin alcohol, oleyl alcohol, hexadecyl alcohol, octyldodecanol alcohol, linoleyl alcohol, linolenyl alcohol, lauryl alcohol and arachidyl alcohol. Fatty acid can be natural or synthetic, saturated, unsaturated, linear, or branched. Non-limiting examples of fatty acid useful in the present compositions are caprylic, isostearic, linoleic, ricinoleic, and oleic acid. Non-limiting examples of the liquid fatty acid ester useful in the present compositions are cetyl octanoate, glyceryl trioctanoate, isopropyl linoleate, isopropyl myristate, isopropyl oleate, ethyl laurate, ethyl linoleate, octyl dodecyl myristate, octyl palmitate, octyl isopelargonate, octyl dodecyl lactate, isotridecyl isononanoate, oleyl oleate, isostearyl myristate, neopentyl glycol dioctanoate, and di(capryl/capric acid) propylene glycol and mixtures thereof. Other suitable esters include triglycerides such as caprylic triglycerides, capric triglyceride, isostearic triglyceride and adipic triglyceride. Non-volatile, straight, and branched silicone oils such as dimethicone and phenyl dimethicone are also useful. Other cosmetically acceptable ingredients like sunscreens include octyl methoxy cinnamate, cinoxate, and 2-ethylphexyl p-dimethyaminobenzoate and the like.

Either one kind or two or more kinds of the cosmetically acceptable liquid oil can be used in the present compositions. It is further contemplated that oil phase materials may not be liquid taken alone, but may, upon heating and/or mixing with other ingredients, provide a component suitable for use as part of the oil phase. Particularly useful emollients include cetyl alcohol, stearyl alcohol and combinations thereof. Typically, the emollients are present in an amount from about 2 to about 25% by weight of the total composition. In embodiments, the emollients are present in an amount from about 5.0 to about 15% by weight of the total composition. In embodiments, a combination of emollients is present, with each individual emollient being present in an amount from about 0.5% to about 10% by weight of the composition.

Suitable antioxidants for use in the oil phase include, but are not limited to 2,6 ditertiarybutyl-4-methyl phenol (commonly known as butylated hydroxytoluene (BHT)), butylated hydroxyanisole (BHA), tocopherol, tocopheryl acetate, ascorbyl palmitate, propyl gallate, and the like. Typically, the one or more antioxidants are present in an amount from about 0.01 to about 10% by weight of the total composition. In embodiments, the antioxidants are present in an amount from about 0.1 to about 2% by weight of the total composition. In embodiments, a combination of antioxidants is present, with each individual antioxidant being present in an amount from about 0.005% to about 1% by weight of the composition.

Suitable preservatives for use in the oil phase include propylparaben, isopropylparaben, butylparaben, and isobutylparaben, and the like. The preservatives in the oil phase typically are present in an amount from about 0.01 to about 5% by weight based on the total composition. In embodiments, preservatives are present in an amount from about 0.05 to about 2% by weight based in the total composition. In embodiments, a combination of preservatives is present, with each individual preservative being present in an amount from about 0.01% to about 1% by weight of the composition.

The oil phase can be prepared by simply adding the ingredients for the oil phase into a tank and heating (e.g., from about 70° C. to about 75° C.) with moderate agitation.

The oil phase can then be added to the aqueous phase (e.g., at a temperature of about 70° C. to about 75° C.) with moderate agitation. The present arbutin compositions can be prepared under an inert, oxygen-free atmosphere as disclosed in U.S. Pat. No. 4,229,427 the entire disclosure of which is incorporated herein by this reference.

The viscosity of the final arbutin composition can be from about 1,000 to about 50,000 centipoise (cps). In embodiments, the viscosity of the final arbutin composition is from about 2,500 to about 35,000 cps. The specific gravity of the final composition can be from about 0.5 and 1.5. In embodiments, the specific gravity of the final arbutin composition is from about 0.90 to about 1.05.

In particularly useful embodiments, the final arbutin composition may have a substantially white color and be a semi-viscous lotion. In particularly useful embodiments, the present compositions have the ability to substantially maintain its color over time. In such embodiments, the present compositions can appear fresh, elegant and professional for their entire shelf life, ensuring patient or consumer confidence in the product.

In embodiments, the present arbutin-containing topical compositions may include:

TABLE 1

| Compound | % of total composition | % by weight of the total composition in Example 1 |
|---|---|---|
| Purified water | About 65 to about 85 | 76.3 |
| Methylparaben | About 0.01 to about 0.5 | 0.1 |
| Edetate disodium | About 0.01 to about 0.5 | 0.1 |
| Glycerin | About 1 to about 15 | 4 |
| Sodium lauryl sulfate | About 0.01 to about 5 | 3 |
| Saponins | About 0.01 to about 5 | 0.05 |
| Lactic Acid 88% | About 0.0 to about 5 | 0.5 |
| Cetyl alcohol | About 1 to about 25 | 6 |
| Stearyl alcohol | About 0.0 to about 25 | 1.35 |
| Propylparaben | About 0.01 to about 0.5 | 0.05 |
| Butylparaben | About 0.00 to about 0.5 | 0.03 |
| Tocopheryl acetate | About 0.01 to about 5 | 0.50 |
| BHT | About 0.01 to about 0.5 | 0.05 |
| Ascorbic Acid | About 0.01 to about 5 | 0.45 |
| Sodium metabisulfite | About 0.01 to about 5 | 0.45 |
| Arbutin | About 0.1 to about 15 | 7.07 |

EXAMPLE 1

Purified water was added to a premix tank under nitrogen gas. The following water phase ingredients were added in the amounts indicated in Table 1 under gentle heat and were homogenously dispersed by mixing at about 70-75° C.: methylparaben, edetate disodium, glycerin, sodium lauryl sulfate, saponins, lactic acid 88%, ascorbic acid, sodium metabisulfite, arbutin. The following oil phase ingredients were mixed in the amounts indicated in Table 1 in a tank at about 70-75° C.: cetyl alcohol, stearyl alcohol, propylparaben, butyl paraben, tocopheryl acetate, and BHT. All contents were then transferred under nitrogen gas into a jacketed tank where the oil phase and water phase were mixed and cooled in order to form an emulsion. All solvents were degassed with nitrogen before use and all formulations and intermediate formulations were degassed. The arbutin-containing formulation was transferred to storage containers that were purged with nitrogen both before and after filling of containers.

The composition identified herein as Example 1A is identical to the composition of Example 1 except that it contains 4% arbutin.

BLENDER EMBODIMENTS

In embodiments, the present compositions are blending compositions designed to be blended with a composition containing an active ingredient (for example, tretinoin) to be applied to the skin. The compositions may include arbutin in a base composition containing water, one or more humectants; one or more emollients, one or more preservatives, one or more chelating agents, one or more pH adjusters, one or more antioxidants, and or more reducing agents.

Suitable preservatives for use in the blending composition further include: benzoic acid, benzyl alcohol, butylparaben, diazolidinyl urea, 2,3-Imidazolidinedione, isopropylparaben, isobutylparaben, methylparaben, propylparaben, sodium butylparaben, sorbic acid, or combinations of these preservatives.

Suitable chelating agents for use in the blending composition further include: citric acid, edetate disodium, ethylenediaminetetraacetic acid, etidronic acid sodium dihydroxyethylglycinate, nitrilotriacetic acid, and combinations of these agents.

Suitable emulsifiers for use in the blending composition further include: cetearyl alcohol, ethoxylated fatty alcohols, PEG-1000 monocetyl ether, alkyl trimethyl ammonium bromide, polyol ester glycerol monostearate, potassium stearate, sodium lauryl sulfate, sodium cetearyl sulfate, saponins, and combinations of these agents.

Suitable humectants for use in the blending composition further include: glycerin, diglycerin, triglycerin, polyglycerin, polypropylene glycol, polyethylene glycol, ethylene glycol, diethylene glycol, triethylene glycol, propylene glycol, dipropylene glycol, hexylene glycol, 1,3-butylene glycol, 1,4-butylene glycol, ethylene glycol monoalkyl ether, diethylene glycol monoalkyl ether, glucose, maltose, sucrose, lactose, xylitose, xylitol, sorbitol, mannitol, maltitol, panthenol, pentaerythritol, hyaluronic acid, and combinations of these humectants.

Suitable pH adjusters for use in the blending composition further include: citric acid, phosphoric acid, lactic acid, glycolic acid, and combinations of these pH adjusters.

Suitable antioxidants for use in the blending composition further include: ascorbyl palmitate, 2,6 ditertiarybutyl-4-methyl phenol, butylated hydroxyanisole, tocopherol, tocopheryl acetate, propyl gallate, and combinations of these antioxidants.

Suitable emollients for use in the blending composition further include: cetyl alcohol, stearyl alcohol, liquid hydrocarbon oil, liquid natural oil, liquid fatty alcohol, liquid fatty acid, liquid fatty acid ester, liquid silicone oil, paste wax, and combinations of these emollients.

Suitable reducing agents for use in the blending composition further include: ascorbic acid, propyl gallate, sodium metabisulfite, and combinations of these reducing agents.

A particularly useful blending composition contains arbutin in a base composition of water, glycerin, cetyl alcohol, PPG-2 myristyl ether propionate, sodium lauryl sulfate, TEA-salicylate, lactic acid, phenyl trimethicone, tocopheryl acetate, sodium metabisulfite, ascorbic acid, methylparaben, saponins, disodium EDTA, BHT and propylparaben.

Suitable blending compositions may also be made in accordance with the ingredients identified in Table 2.

TABLE 2

| Compound | % of total composition | % by weight of the total composition in Example 2 |
|---|---|---|
| Purified water | About 70 to about 85 | Purified water 64.35 |
| Preservatives | About .01 to about 1.5 | methylparaben 0.15 propylparaben 0.05 |
| Chelating Agent | About .01 to about 0.5 | disodium EDTA 0.1 |
| Humectants | About 1 to about 10 | Glycerin 12.0 |
| Anionic Surfactants | About .01 to about 5 | Saponins 0.05 |
| Emulsifiers | About 0.01 to about 5 | sodium lauryl sulfate 2.0 Triethanolamine Salicylate 1.0 |
| C12-C18 Alkyl Alcohols | About 2 to about 50 | cetyl alcohol 8.00 |
| Antioxidants | About .01 to about 10 | tocopheryl acetate 0.5 butylated hydroxytoluene 0.03 |
| Reducing Agents | About .01 to about 5 | sodium metabisulfite 0.45 Ascorbic acid 0.25 |
| Emollient | About 1 to about 10 | polyoxypropylene (2) myristyl ether propionate 3.0 Phenyl Trimethicone/dimethyl polysiloxane 0.5 |
| pH adjuster | About 0.01 to about 5 | lactic acid 0.5 |
| arbutin | About 5 to about 10% | 7.07 |

The composition identified herein as Example 2A is identical to Example 2 except that it contains 4% arbutin.

The present compositions can be packaged in any type of container, such as, for example, bottles, tubes, vials and the like. The compositions can be dispensed by any suitable means such as, for example, pumping or simply squeezing from a tube.

The present arbutin-containing compositions can be applied to an area of the skin of a user daily in an amount sufficient to cause skin lightening. In embodiments, the present arbutin-containing compositions are applied in an amount from about 1 milligram per square centimeter of skin to about 15 mg/cm².

EXAMPLE 3

Use of the Presently Described Compositions and Systems

Ten volunteers between the ages of 18 and 60 years of age enrolled in the study. Volunteers included in the study were of Asian or Caucasian descent with a Fitzpatrick phototype III or above. Enrolled subjects were free of any systemic or dermatologic disorder, including a known history of allergies or other medical conditions which, in the opinion of the Medical Investigator, could interfere with the conduct of the study, interpretation of results, or increase the risk of adverse reactions. Moreover, volunteers had no clinically significant abnormal findings, based on their medical history, which may have affected study participation as determined by the investigator. Impaneled female volunteers were not pregnant (as assessed with a urine pregnancy test at the start of the study and every 4 weeks thereafter) and agreed to use suitable contraceptive methods throughout the duration of the study. All volunteers were willing to refrain from using any medications, moisturizers, sunscreens, fragrances or new personal care products/laundry detergents on the back for the duration of the study and were also willing to avoid sun exposure, on the back (ie, sunbathing), as best as possible and refrain from using tanning booths for the study duration. Furthermore, subjects agreed to avoid swimming for the entire study.

Volunteers that were excluded from the study were females that were pregnant, breast feeding, or have been trying to become pregnant for three months prior to the study or anticipate becoming pregnant during the experimental period. Also excluded were individuals with any known allergies or sensitivity to any ingredients in the test products or other clinical supplies that were used in the study. Volunteers were also excluded if they had received prior cosmetic procedures on the back (mole removal, laser resurfacing, chemical peel, dermabrasion, etc.) within six months of the start of the study. Individuals with sunburn on their backs or those whose activities involve excessive or prolonged exposure to sunlight were also excluded. Also excluded were subjects taking medications which might interfere with the test results, including the use of steroidal/non-steroidal anti-inflammatory drugs, antibiotics or antihistamines. Candidates with uncontrolled systemic disease, known infection with human immunodeficiency virus, active atopic dermatitis/eczema, psoriasis or history of any form of cancer were also excluded. Volunteers who were under treatment for asthma or diabetes or had a known sensitivity to skin lightening products or had a history of sensitivity to cosmetics or personal care products were also excluded.

All volunteers reported to the clinical site every day, excluding weekends, for application of study products in an open label, un-blinded fashion. Study products and dosing were as follows:

| Product | Ingredient | Dosage |
|---|---|---|
| Example 1 | 7% Arbutin | 10 mg/cm² |
| Example 2 | 7% Arbutin | 10 mg/cm² or 5 mg/cm²** |
| Example 1A | 4% Arbutin | 10 mg/cm² |
| Example 2A | 4% Arbutin | 10 mg/cm² |
| Bleaching and correcting cream* | 4% Hydroquinone | 10 mg/cm² |
| Blender* | 4% Hydroquinone | 10 mg/cm² or 5 mg/cm²** |
| Toner* | | 10 μL/cm² |
| Cationic Toner*** | | 10 μL/cm² |
| 0.025% Tretinoin | | 5 mg/cm² |

*commercially available from OMP, Inc., Long Beach, CA.
**when used with 0.025% Tretinoin
***See Example 1 of Published U.S. Patent Application 2007/0269534A1 (the entire content of which is incorporated herein by this reference).

All subjects had 2 cm² squares demarcated on their backs, with a plastic template adhered to the skin, for identification of treatment sites. Subjects were treated with the formulation of Example 1, the formulation of Example 2, bleaching and correcting cream and Blender alone or as part of a system. Each regimen is described below:

Example 1A Formulation: 20 mg of product were applied once daily, Monday thru Friday at the clinical site, for 8-weeks.

Example 2A Formulation: 20 mg of product were applied once daily, Monday thru Friday at the clinical site, for 8-weeks.

Example 1 Formulation: 20 mg of product were applied once daily, Monday thru Friday at the clinical site, for 8-weeks.

Example 2 Formulation: 20 mg of product were applied once daily, Monday thru Friday at the clinical site, for 8-weeks.

Bleaching and Correcting Cream: 20 mg of product were applied once daily, Monday thru Friday at the clinical site, for 8-weeks.

Blender: 20 mg of product were applied once daily, Monday thru Friday at the clinical site, for 8-weeks.

The Presently Described System: 20 μl of cationic toner were applied first, then allowed to absorb for 5 minutes. 20 mg of the Example 1 formulation were applied next and allowed to absorb for 5 minutes. Finally, 10 mg of the Example 2 formulation were mixed with 10 mg of 0.025% Tretinoin and then applied to the skin. The presently described System was applied once daily, Monday thru Friday at the clinical site, for 8-weeks.

Comparative System: 20 μl of toner were applied first, then allowed to absorb for 5 minutes. 20 mg of bleaching and correcting cream were applied next and allowed to absorb for 5 minutes. Finally, 10 mg of blender were mixed with 10 mg of 0.025% tretinoin and then applied to the skin. The Comparative System was applied once daily, Monday thru Friday at the clinical site, for 8-weeks.

The safety of the formulations of Example 1 and Example 2 was assessed via Repeated Insult Patch Testing on 49 volunteers, in a separate study. All products used in the study presented herein were evaluated for safety through investigator scoring of the application sites at baseline, 4- and 8-weeks. In addition, all treatment sites were visually inspected daily, during routine application of test products, for any reactions. Skin lightening was assessed via use of the Minolta CR-300 Chromameter® at baseline, 4- and 8-weeks. Very briefly, The Chromameter measures color changes in the skin through three different color parameters. The L* parameter measures color changes from black to white, the a* parameter measures red to green and the b* parameter measures yellow to blue. An increase in L* and a decrease in b* parameters is indicative of skin lightening. The L* parameter, however, can be affected by erythema or skin irritation, thus potentially giving false positive or false negative readings. The b* parameter measures skin lightening only and is not affected by erythema or irritation. Data were reported as mean change in Chromameter® (b* value) readings from baseline. Skin lightening can also be measured via the Chromameter® L* value and/or the Individual Typology Angle (ITA°), which is calculated using the Chromameter® b* and L* values. The Individual Typology Angle is described in Chardon A, Cretois I, Hourseau C., Skin color typology and suntanning pathways. Int J Cosmet Sci 1991; 13:191-208, the entire disclosure of which is incorporated herein by this reference.

Both the formulations of Example 1 and Example 2 were subjected to RIPT and in-use safety testing. RIPT testing showed that 1 of 49 volunteers had a moderate reaction to the Formulation of Example 1. This is not surprising as the Formulation of Example 1 was applied under semi-occlusive patch. Moreover, it is likely that the SLS in the formula caused the irritation rather than the arbutin. On the other hand, in-use safety testing was conducted under open conditions (no patch) and resulted in no skin reactions.

When comparing application of 4% arbutin (the formulations of Examples 1A and 2A) versus 7% arbutin (the formulations of Examples 1 and 2), we see that 7% arbutin yields superior skin lightening versus 4% arbutin, at 8-weeks, as confirmed by Chromameter® b* parameter values (See FIGS. 1A and 1B). Hence, the skin lightening efficacy of arbutin, in the formulations of Examples 1 and 2 base formulas, is dose dependant. Chromameter b* values also suggest that both the formulations of Examples 1 and 2 may be better skin lighteners than the hydroquinone-based bleaching and correcting cream and Blender formulas (See FIGS. 2A and 2B). Concurrent use of a cationic toner and 0.025% tretinoin with the formulations of Examples 1 and 2, as a system, showed greater skin lightening efficacy as compared to the formulations of Examples 1 and 2 alone (See FIG. 3). Moreover, the presently described system was shown to be a virtually equally effective skin lightening system as the Comparative System comprising a toner, bleaching and correcting cream (4% hydroquinone), Blender (4% hydroquinone) and 0.025% Tretinoin (See FIG. 4).

As seen from the data presented herein, 7% Arbutin can be equally as efficacious as 4% hydroquinone, at lightening relatively non-photoexposed skin, when incorporated into formulas similar to the commercially available bleaching and correcting cream and Blender base formulas. This is an unpredictable finding given that the tyrosinase inhibiting potency of arbutin, in human melanocyte cultures, was previously found to be one-hundredth that of hydroquinone. (See, Maeda K, Fukuda M. Arbutin: mechanism of its depigmenting action in human melanocyte culture. *J Pharmacol Exp Ther*. February 1996; 276(2):765-769.) Hence the presently described arbutin formulations facilitate the enhanced skin lightening efficacy of arbutin. Without wishing to be bound to any theory, it is believed that the presently described formulations enhance the transdermal penetration of arbutin (the molecular weight of which is more than twice that of hydroquinone) which may contribute to the improved skin lightening efficacy of 7% arbutin under the study conditions described herein.

Figure 1A:
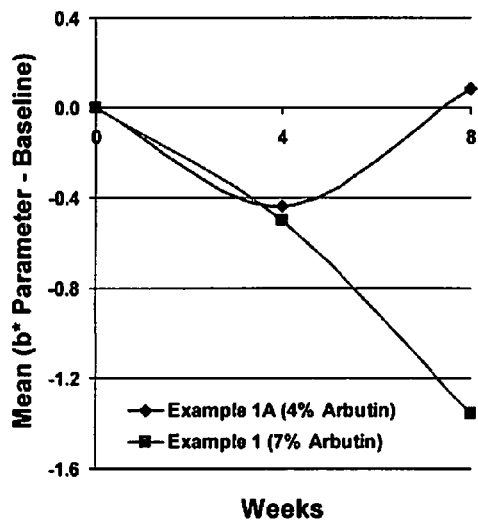
FIGS. 1A and 1B show arbutin-mediated skin lightening is dose dependant. Skin lightening for 4- and 7% Arbutin formulations of Examples 1 and 2 was determined using the b* parameter of the Minolta Chromameter®. The graphs were made by subtracting the baseline Chromameter b* value from the 4- and 8-week b* values for each volunteer and then averaging the delta b* for the study population at each time point. Hence, the graphs display the mean delta b* over time. A decrease in Chromameter b* parameter means skin lightening. (N=10).
Figure 1B:
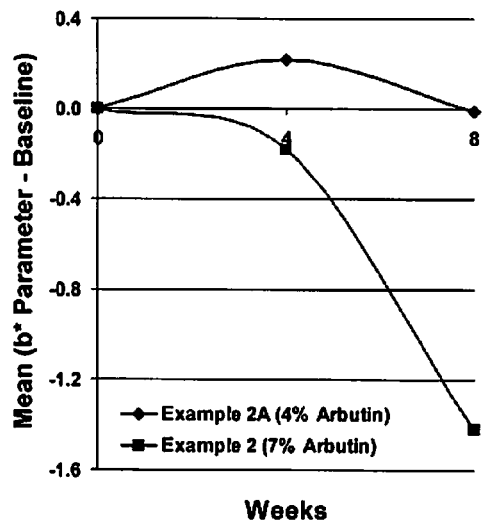
Figure 2A:
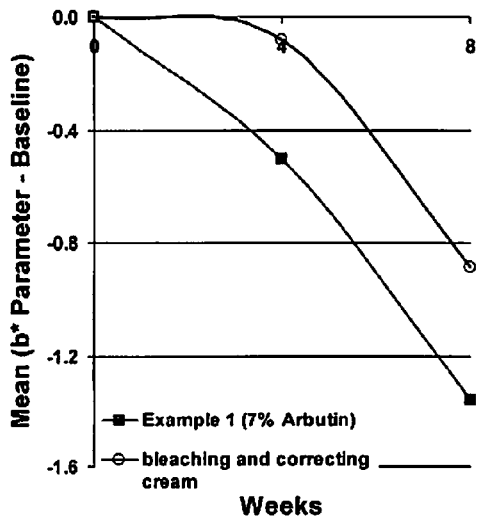
FIGS. 2A and 2B show the skin lightening efficacy of the formulations of Examples 1 and 2 versus bleaching and correcting cream (4% HQ) and blender (4% HQ) skin lightening efficacy. Skin lightening was determined using the b* parameter of the Minolta Chromameter®. The graphs were made by subtracting the baseline Chromameter b* value from the 4- and 8-week b* values for each volunteer and then averaging the delta b* for the study population at each time point. Hence, the graphs display the mean delta b* over time. A decrease in Chromameter b* parameter means skin lightening. (N=10).
Figure 2B:
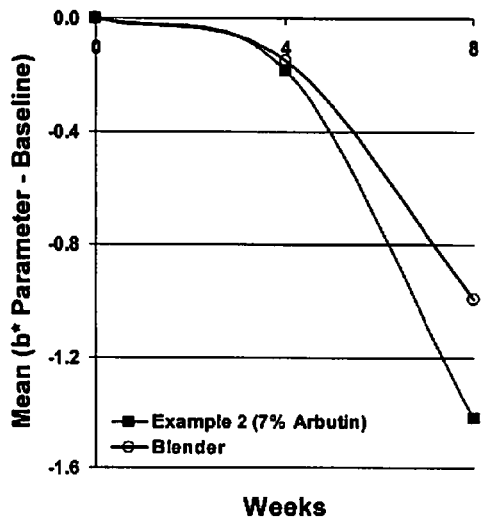
Figure 3:
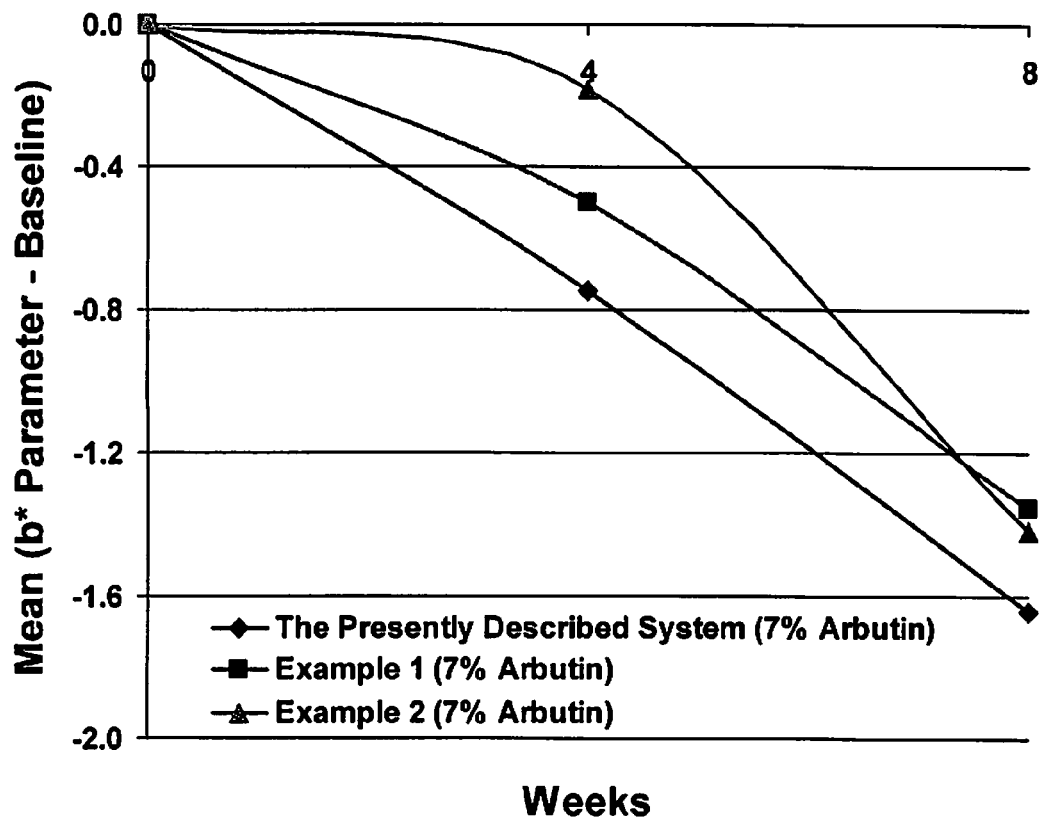
FIG. 3 show simultaneous use of a cationic toner and 0.025% Tretinoin with the formulations of Examples 1 and 2, in a system, affords improved skin lightening compared to the formulations of Examples 1 and 2 alone. Skin lightening was determined using the b* parameter of the Minolta Chromameter®. The graphs were made by subtracting the baseline Chromameter b* value from the 4- and 8-week b* values for each volunteer and then averaging the delta b* for the study population at each time point. Hence, the graphs display the mean delta b* over time. A decrease in Chromameter b* parameter means skin lightening. (N=10).
Figure 4:
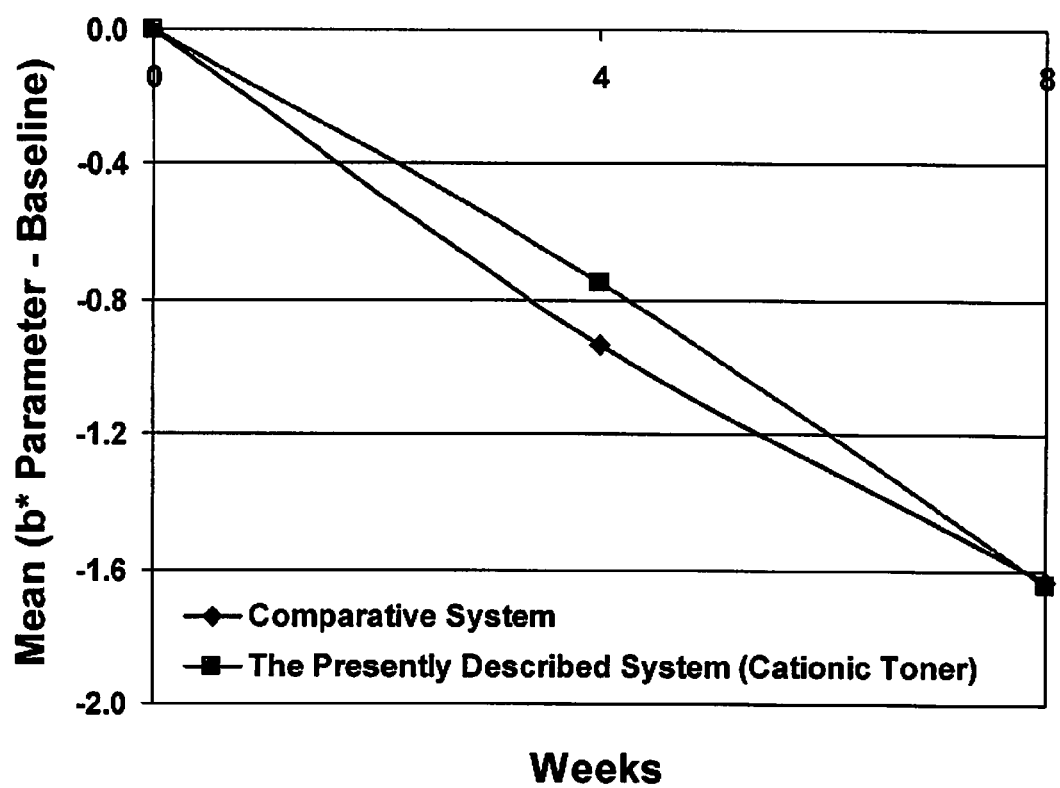
FIG. 4 shows the presently described System (including the use of formulations containing 7% arbutin) skin lightening efficacy versus the Comparative System (4% hydroquinone) skin lightening efficacy. Skin lightening was determined using the b* parameter of the Minolta Chromameter®. The graphs were made by subtracting the baseline Chromameter b* value from the 4- and 8-week Chromamete b* values for each volunteer and then averaging the delta b* for the study population at each time point. Hence, the graphs display the mean delta b* over time. A decrease in Chromameter b* parameter means skin lightening. (N=10).

As the foregoing data shows, the present arbutin-containing compositions provided skin lightening effects at 8 weeks that was at least 85% as efficacious (with regard to skin lightening, when used alone or in a system as measured by Chromameter® b* parameter values) as the hydroquinone-containing compositions to which they were compared. In some cases the present arbutin-containing compositions provided better skin lightening effects at 8 weeks (as measured by Chromameter® b* parameter values) than the hydroquinone-containing compositions to which they were compared.

It will be understood that various modifications may be made to the embodiments disclosed herein. Therefore, the above description should not be construed as limiting, but merely as exemplifications of embodiments. Those skilled in art will envision other modifications within the scope and spirit of the claims appended hereto.

The invention claimed is:

1. An arbutin-containing composition comprising:
   arbutin in an amount from about 5% to about 10% by weight of the total composition;
   a preservative in an amount from about 0.01 to about 5% by weight of the total composition;
   a chelating agent in an amount from about 0.01 to about 5% by weight of the total composition;
   a humectant in an amount from about 1 to about 20% by weight of the total composition;
   an emulsifier in an amount from about 1 to about 20% by weight of the total composition;

a pH adjustment agent in an amount from about 0.01 to about 5% by weight of the total composition; and a reducing agent in an amount from about 0.1 to about 10% by weight of the total composition, wherein the composition is at least 85% as efficacious with regard to skin lightening, when used alone or in a system as measured by Chromameter® b* parameter values as a substantially corresponding composition containing hydroquinone in an amount from about the same molar amount to about 1.5 times the molar amount of arbutin.

2. The arbutin-containing composition of claim 1 comprising an oil phase comprising an emollient, a preservative and an antioxidant.

3. The arbutin-containing composition of claim 2 comprising emollient in an amount from about 2 to about 25% by weight of the total composition;

preservative in an amount from about 0.01 to about 5% by weight based on the total composition; and antioxidant in an amount from about 0.1 to about 2% by weight of the total composition.

4. The arbutin-containing composition of claim 1, comprising 7% arbutin.

\* \* \* \* \*